(12) United States Patent
Dougal

(10) Patent No.: US 9,314,302 B2
(45) Date of Patent: Apr. 19, 2016

(54) COSMETIC USES OF ELECTROMAGNETIC RADIATION

(75) Inventor: Gordon Rex Paterson Dougal, Durham (GB)

(73) Assignee: Virulite LLC, Costa Mesa, CA (US)

( * ) Notice: Subject to any disclaimer, the term of this patent is extended or adjusted under 35 U.S.C. 154(b) by 1620 days.

(21) Appl. No.: 11/570,993

(22) PCT Filed: Jun. 21, 2005

(86) PCT No.: PCT/GB2005/002433
§ 371 (c)(1),
(2), (4) Date: Sep. 25, 2008

(87) PCT Pub. No.: WO2006/000757
PCT Pub. Date: Jan. 5, 2006

(65) Prior Publication Data
US 2009/0012508 A1    Jan. 8, 2009

(30) Foreign Application Priority Data
Jun. 24, 2004    (GB) .................................. 0414113.1

(51) Int. Cl.
| | | |
|---|---|---|
| A61B 19/00 | (2006.01) | |
| A61B 18/18 | (2006.01) | |
| A61B 18/20 | (2006.01) | |
| A61B 18/00 | (2006.01) | |

(52) U.S. Cl.
CPC ....... *A61B 18/203* (2013.01); *A61B 2018/0047* (2013.01); *A61B 2018/00452* (2013.01)

(58) Field of Classification Search
CPC ..................... A61B 18/18; A61B 2018/00452; A61B 2018/0047; A61B 2018/1807; A61N 5/06; A61N 5/0616; A61N 5/062; A61N 2015/065; A61N 2015/0651; A61N 2015/0652
USPC ............ 606/3, 8–12; 607/88–91, 94, 96, 100, 607/108–111; 128/898
See application file for complete search history.

(56) References Cited

U.S. PATENT DOCUMENTS

| | | | |
|---|---|---|---|
| 3,473,868 | A | 10/1969 | Newman et al. |
| 3,533,683 | A | 10/1970 | Stark et al. |
| 4,641,349 | A | 2/1987 | Flom et al. |
| 4,858,609 | A | 8/1989 | Cole |

(Continued)

FOREIGN PATENT DOCUMENTS

| | | |
|---|---|---|
| DE | 4003477 | 8/1991 |
| DE | 29820468 | 4/2000 |

(Continued)

OTHER PUBLICATIONS

Final Rejection, for U.S. Appl. No. 11/652,212, Aug. 27, 2013.*
Non-Final Rejection, for U.S. Appl. No. 11/652,212, Dec. 30, 2012.*
Dougal G. and Kelly P., "A pilot study of treatment of herpes labialis with 1072 nm narrow waveband light," Clinical and Experimental Dermatology 26:2 (Mar. 1, 2001) 149-154.
Agaiby A.D., et al., "Laser modulation of angiogenic factor production by T-lymphocytes," Lasers in Surgery and Medicine 26 (2000) 357-363.
Mohanty S.K., et al., "Comet assay measurements of DNA damage in cells by laser microbeams and trapping beams with wavelengths spanning a range of 308 nm to 1064 nm," Radiation Research 157:4 (Apr. 2004) 378-385.
International Search Report, PCT/GB2005/002433, Aug. 18, 2005.
Abergel et al. "Laser Treatment of Keloids: A Clinical Trial and an In Vitro Study with Nd:YAG Laser" *Lasers in Surgery and Medicine* 4:291-295 (1984).

(Continued)

*Primary Examiner* — Ahmed Farah

(57) ABSTRACT

A method of cosmetically treating a superficial area of mammalian skin by irradiating the skin with a source of divergent electromagnetic radiation of between 900 nm to 1500 nm, and use of electromagnetic radiation of specified wavelengths. The cosmetic treatment includes reducing or alleviating or removing or diminishing wrinkles or fine lines, rejuvenating skin, retarding or reversing visible signs of aging, improving skin elasticity, tone, texture and appearance and beautifying facial, breast, arm, buttock, thigh, stomach or neck skin.

14 Claims, 9 Drawing Sheets

(56) References Cited

U.S. PATENT DOCUMENTS

| | | |
|---|---|---|
| 4,878,891 A | 11/1989 | Judy et al. |
| 4,917,084 A | 4/1990 | Sinofsky |
| 4,930,504 A | 6/1990 | Diamantopoulos et al. |
| 4,951,663 A | 8/1990 | L'Esperance, Jr. |
| 5,066,291 A | 11/1991 | Stewart |
| 5,259,380 A | 11/1993 | Mendes et al. |
| 5,348,551 A | 9/1994 | Spears et al. |
| 5,445,146 A | 8/1995 | Bellinger |
| 5,464,436 A | 11/1995 | Smith |
| 5,478,239 A | 12/1995 | Fuerst et al. |
| 5,500,009 A | 3/1996 | Mendes et al. |
| 5,507,716 A | 4/1996 | LaBerge et al. |
| 5,527,350 A | 6/1996 | Grove et al. |
| 5,630,811 A | 5/1997 | Miller |
| 5,658,323 A | 8/1997 | Miller |
| 5,707,403 A | 1/1998 | Grove et al. |
| 5,743,901 A | 4/1998 | Grove et al. |
| 5,784,145 A | 7/1998 | Ghodse et al. |
| 5,805,267 A | 9/1998 | Goldman |
| 5,818,048 A | 10/1998 | Sodickson et al. |
| 5,849,035 A | 12/1998 | Pathak et al. |
| 5,868,731 A | 2/1999 | Budnik et al. |
| 5,913,883 A | 6/1999 | Alexander et al. |
| 5,989,245 A | 11/1999 | Prescott |
| 6,027,495 A | 2/2000 | Miller |
| 6,063,108 A * | 5/2000 | Salansky et al. .......... 607/89 |
| 6,091,546 A | 7/2000 | Spitzer |
| 6,113,237 A | 9/2000 | Ober et al. |
| 6,149,272 A | 11/2000 | Bergner et al. |
| 6,179,830 B1 | 1/2001 | Kokubu |
| 6,193,373 B1 | 2/2001 | Apple et al. |
| 6,299,308 B1 | 10/2001 | Voronka et al. |
| 6,334,683 B2 | 1/2002 | Apple et al. |
| 6,358,272 B1 | 3/2002 | Wilden |
| 6,471,716 B1 | 10/2002 | Pecukonis |
| 6,663,659 B2 | 12/2003 | McDaniel |
| 6,887,260 B1 * | 5/2005 | McDaniel .......... 607/88 |
| 6,986,765 B2 | 1/2006 | Sumiya et al. |
| 7,060,061 B2 * | 6/2006 | Altshuler et al. .......... 606/3 |
| 7,549,984 B2 | 6/2009 | Mathis |
| 7,730,893 B2 * | 6/2010 | Dougal .......... 128/898 |
| 2001/0028309 A1 | 10/2001 | Torch |
| 2003/0058492 A1 | 3/2003 | Wakiyama |
| 2004/0122491 A1 | 6/2004 | Strong |
| 2004/0225340 A1 | 11/2004 | Evans |
| 2005/0024853 A1 | 2/2005 | Thomas-Benedict |
| 2005/0187579 A1 | 8/2005 | Danek et al. |
| 2005/0234383 A1* | 10/2005 | Dougal .......... 604/5.02 |
| 2006/0271131 A1 | 11/2006 | Passy et al. |
| 2007/0129778 A1* | 6/2007 | Dougal .......... 607/88 |

FOREIGN PATENT DOCUMENTS

| | | |
|---|---|---|
| DE | 10049068 | 9/2001 |
| DE | 10201904 | 7/2003 |
| DE | 10237620 | 3/2004 |
| EP | 0533585 A1 | 3/1993 |
| EP | 0695559 | 2/1996 |
| EP | 1 021 223 B1 | 10/2004 |
| GB | 2415387 | 12/2005 |
| JP | 2000-517211 A | 12/2000 |
| JP | 2001-519217 A | 10/2001 |
| KR | 20-0297648 | 12/2002 |
| WO | WO 2006/028465 | 2/1996 |
| WO | WO 97/47993 | 12/1997 |
| WO | WO 98/23329 A1 | 6/1998 |
| WO | WO 99/19024 A | 4/1999 |
| WO | WO 99/19024 A1 | 4/1999 |
| WO | WO 01/30292 A2 | 5/2001 |
| WO | WO 2004/000150 | 12/2003 |
| WO | WO 2006/108093 A2 | 10/2006 |
| WO | WO 2006/108093 A3 | 10/2006 |
| WO | WO 2009/038720 A2 | 3/2009 |

OTHER PUBLICATIONS

Abergel et al. "Nonthermal Effects on Nd:YAG Laser on Biological Functions of Human Skin Fibroblasts in Culture" *Lasers in Surgery and Medicine* 3:279-284 (1984).

Agaiby et al. "Laser modulation of angiogenic factor production by T-lymphocytes" *Lasers in Surgery and Medicine* 26:357-363 (2000).

Almeida-Lopes et al. "Comparison of the Low Level Laser Therapy Effects on Cultured Human Gingival Fibroblasts Proliferation Using Different Irradiance and Same Fluence" *Lasers in Surgery and Medicine* 29:179-184 (2001).

Castro et al. "Effects of the Nd:YAG Laser on DNA Synthesis and Collagen Production in Human Skin Fibroblast Cultures" *Annals of Plastic Surgery* 11(3):214-222 (1983).

Davis, Christopher C. *Laser & Electro-Optics* Cambridge University Press, p. 289 (1996).

Dougal et al. "A pilot study of treatment of herpes labialis with 1072 nm narrow waveband light" *Clinical and Experimental Dermatology* 25:149-154 (2001).

International Search Report for PCT/GB2005/002433; date of mailing Aug. 18, 2005.

Kreisler et al. "Low Level 809-nm Diode Laser Induced In Vitro Stimulation of the Proliferation of Human Gingival Fibroblasts" *Lasers in Surgery and Medicine* 30:365-369 (2002).

Loevschall et al. "Effect of Low Level Diode Laser Irradiation of Human Oral Mucosa Fibroblasts in Vitro" *Lasers in Surgery and Medicine* 14:347-354 (1994).

Mohanty et al. Comet Assay Measurements of DNA Damage in Cells by Laser Microibeams and Trapping Beams with Wavelengths Spanning a Range of 308 NM to 1064 NM' *Radiation Research* 157(4):378-385 (2002).

Mokhtar et al. "Double-Blind, Placebo-Controlled Investigation of the Effect of Combined Phototherapy/Low Intensity Laser Therapy Upon Experimental Ischaemic Pain in Humans" *Lasers in Surgery and Medicine* 17:74-81 (1995).

Pereira et al. "Effect of Low-Power Laser Irradiation on Cell Growth and Procollagen Synthesis of Cultured Fibroblasts" *Lasers in Surgery and Medicine* 31:263-267 (2002).

Sakihama, Hideki "Effect of a Helium-Neon Laser on Cutaneous Inflammation" *The Kurame Medical Journal* 42:299-305 (1995).

Vecchio et al. "A Double-Blind Study of the Effectiveness of Low Level Laser Treatment of Rotator Cuff Tendinitis" *British Journal of Rheumatology* 32:740-742 (1993).

International Preliminary Report on Patentability and Written Opinion of the International Searching Authority for International Application No. PCT/EP2010/054762; date of mailing: Oct. 27, 2011; 16 pages. 8.

International Search Report and Written Opinion of the ISA for International Application No. PCT/EP2010/054762; date of mailing Jun. 28, 2010; 16 pages.

Spicer et al.; Lasers in Dermatology, Journal of the American Academy of Dermatology, Jan. 1996.

Steller et al.; Lasers in Surgery, Laser Applications in Medicine and Biology, vol. 2., 1974 pp. 246-249.

Notification of Transmittal of the International Search Report and the Written Opinion of the International Searching Authority, or the Declaration corresponding to International Application No. PCT/GB2006/002153 mailed Nov. 10, 2006.

International Preliminary Report on Patentability and Written Opinion dated Jan. 27, 2011 for PCT/GB2009/050848.

Notification of Transmittal of the ISR and the Written Opinion of the ISA, or the Declaration corresponding to International Application No. PCT/GB2006/002153 mailed Nov. 10, 2006.

Definition of Solid-State from Whatis.com, retrieved from the internet on Oct. 21, 2012 at http://encyclpedia2.thefreedictionary.com/Solid+state+(electronics).

* cited by examiner

SECTION A-A

FIGURE 10
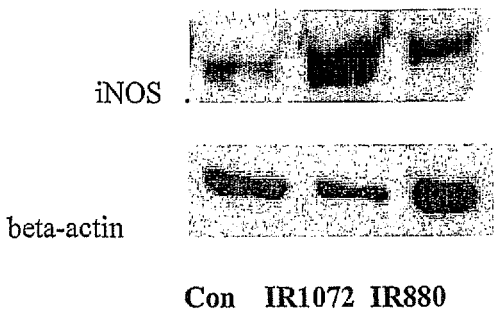
iNOS
beta-actin
Con   IR1072   IR880
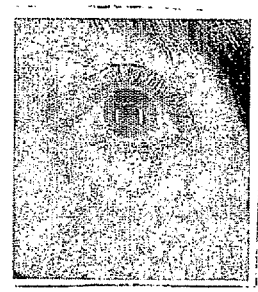
FIGURE 11A
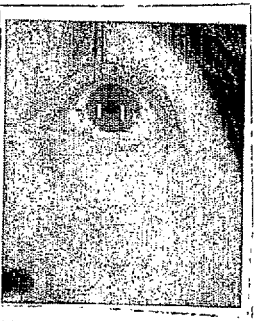
FIGURE 11B
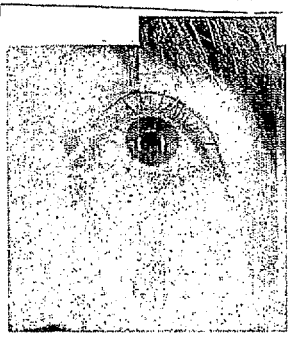
FIGURE 11C FIGURE 13A
FIGURE 13B
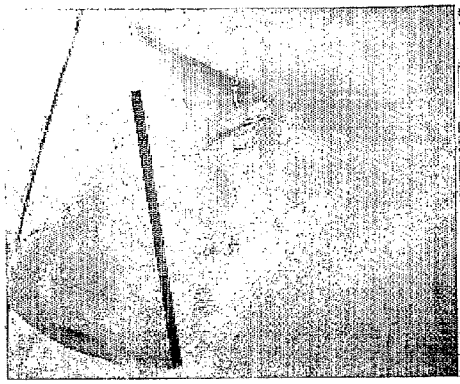
FIGURE 14A
FIGURE14B
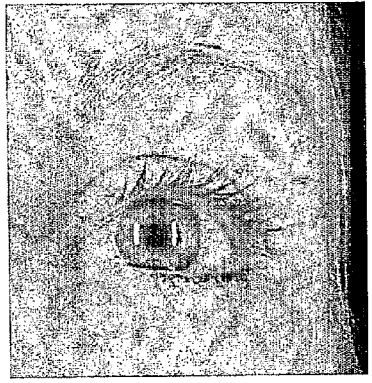
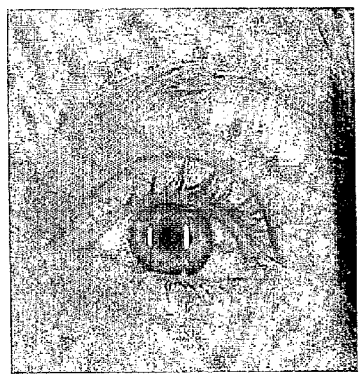
FIGURE 14C

COSMETIC USES OF ELECTROMAGNETIC RADIATION

RELATED APPLICATION

This application is a national phase application of PCT Application PCT/GB2005/002433, filed Jun. 21, 2005, and published in English on Jan. 5, 2006 as International Publication No. WO 2006/000757, which claims priority from British Application No. 0414113.1, filed Jun. 24, 2004. These disclosures are hereby incorporated by reference herein in their entirety.

The present invention relates to the cosmetic use of electromagnetic radiation for the reduction or alleviation or removal or diminishing of wrinkles or fine lines, especially but not exclusively facial and neck wrinkles and other signs of aging. The present invention also provides the use of electromagnetic radiation for generally rejuvenating skin, retarding signs of aging and improving skin elasticity, tone and appearance. The invention also provides for a method of treating skin so as to reduce or alleviate or retard or reverse visible signs of aging and for beautifying skin and an apparatus for effecting such cosmetic treatments.

BACKGROUND

In young skin, the collagen just beneath the surface of the skin forms an organised lattice with good elasticity and flexibility. As women go through menopause and men age, both experience increased skin wrinkling and decreased skin thickness. During aging, the collagen changes its structure impacting negatively on the cosmetic appearance of the skin. The change in collagen may also be accelerated by prolonged exposure to the sun's UV rays. Billions of pounds are spent annually on the cosmetic industry and it is estimated that the average woman spends around £800 per annum on skin care products and cosmetics.

It is known from the prior art to use chemical peels or cosmetic preparations, typically in the form of creams, to prevent or mitigate wrinkles and as anti-aging agents. Such preparations may contain synthetic or naturally occurring plant and/or animal products. The compositions are applied topically and usually on a regular basis in order to maximise their effects. However, there is limited evidence that even persistent use of such compositions alleviate the visible signs of aging.

As an alternative to cosmetic preparations and surgical facelifts, it is known to use a source of low-level electromagnetic radiation to achieve photochemical responses in the skin, commonly referred to as biostimulation. Biostimulation depends upon the concept of enhanced replication and synthesis, which results in increased collagen production, increased fibroblast stimulation or increased DNA synthesis. The light energy is absorbed in cytochromes and porphyrins within cell mitochondria and cell membranes producing a small amount of singlet oxygen. Typically, patients require four to six sessions for acute conditions and six to eight treatments for chronic conditions. This type of treatment is both prolonged and expensive.

Since the 1990s, lasers have been used for skin resurfacing and wrinkle removal. Wrinkle removal is an aggressive technique where tissue is removed layer-by-layer, invading the dermis and effectively inducing second-degree burn. Heat is deposited in the dermis shrinking the collagen and tightening the skin. The laser induces denaturing of the collagen in the dermis and the formation of cross-links, which result in a tightening effect stretching the skin, thus reducing or removing the wrinkles. This process is referred to a thermolysis and thermal heating of tissues is a prerequisite for the therapy, it is thought that the thermal threshold for thermolysis is about 70° C. However, the problem with traditional laser treatment is that the patient may suffer burns and so have a weeping skin, scabs and redness for many weeks post treatment. In addition a high incidence of hyperpigmentation has been reported following $CO_2$ laser wrinkle removal treatment.

There is therefore a need for an alternative, effective and safe method of reducing or alleviating or removing or diminishing wrinkles or fine lines, rejuvenating skin, retarding the signs of aging and improving skin elasticity, tone and appearance and for generally beautifying skin.

BRIEF SUMMARY OF THE DISCLOSURE

According to a first aspect of the invention there is provided a method of cosmetically treating a superficial area of mammalian skin comprising irradiating the skin with a source of divergent electromagnetic radiation of between 900 nm to 1500 nm.

Reference herein to "cosmetically treating" includes reducing or alleviating or removing or diminishing wrinkles or fine lines, rejuvenating skin, retarding or reversing the visible signs of aging, improving skin elasticity, tone, texture and appearance and generally beautifying.

Reference herein to "skin" includes the outermost epidermis, basal layer and dermis of the face, breast, arm, buttock, thigh, stomach or neck.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Preferably the divergent light is between 10° to 50°. By divergent it meant that the electromagnetic radiation emitted from the electromagnetic source has a divergent half angle of at least 5°. Preferably divergence of the electromagnetic radiation is in the range 15° to 25° half angled divergent.

Thus it will be appreciated that the method of the present invention does not include the use of lasers as the source of electromagnetic radiation.

It has now been surprisingly established that low intensity electromagnetic radiation of small bandwidth (preferably around 10 nm to 120 nm and more preferably 50 nm) is effective in cosmetically treating skin. It is postulated that the way in which the electromagnetic radiation effects its action is by way of energy transmission through cellular components/organelles, enzymes such as but not limited to inducible nitric oxide synthase (iNOS). A water molecule that has a range of electromagnetic radiation wavelengths passed through it will produce several transmission peaks. These transmission peaks are associated with the preferred therapeutic electromagnetic radiation wavelength range of the invention and thus implies a role for the water molecule in the general mechanism of action.

Preferably, the wavelength of the electromagnetic radiation is centred around any one or more of the specified wavelengths selected from the group comprising 940 nm, 950 nm, 1040 nm, 1060 nm, 1072 nm and 1267 nm.

Our studies have shown that wavelengths centred around those wavelengths specified above and especially around single restricted bandwidth light centred at 1072 nm or 1267 nm are particularly effective at reducing wrinkle length and area. It is of note that these two wavelengths correspond to the peak emission wavelengths of a water molecule light transmission profile and thus we believe that the mechanism of action is related to water and possibly cell membranes.

Our studies have also shown that 1072 nm and 880 nm elicit opposing effects upon lymphocyte viability ex vivo, the former being protective and the latter wavelength cytotoxic. Furthermore, we provide evidence that 1072 nm protects against UV-mediated lymphotoxicity.

Preferably, the electromagnetic radiation is continuous or pulsed.

Preferably, when the electromagnetic radiation is continuous the intensity is at least 500 $\mu$Watts/cm$^2$ and up to 500 mWatts/cm$^2$.

Preferably when the electromagnetic radiation is pulsed the intensity is at least 500 $\mu$Watts/cm$^2$ peak power and the average power is up to 500 mWatts/cm$^2$. The average power is the peak power multiplied by the proportion of the total time that the radiation is applied. For instance if the peak power is 500 $\mu$Watts/cm$^2$ and is pulsed for 10 $\mu$seconds at a frequency of 600 Hz then the average power is 30 $\mu$Watts/cm$^2$.

Prior art methods which rely on thermal warming specify a lower limit of 0.5 Watts/cm$^2$ the present invention which seeks to avoid any thermal effects operates below this level.

Preferably when the electromagnetic radiation is pulsed the average power of the intensity is in the region of 50-100p Watts/cm$^2$.

We have found that the power may suitably range from 500 $\mu$Watts/cm$^2$ peak to 500 milliwatts/cm$^2$ continuous or peak power when applied to the skin. Typically 20 mWatts/cm$^2$ are used on skin but this value is dependent on how fat or muscular the subject is and thus how deep the wrinkle lies.

Preferably when the electromagnetic radiation is pulsed it is applied for periods of at least 10-15 $\mu$seconds and more preferably is applied at a frequency/repetition rate in the range 300-900 Hz more preferably still the frequency/repetition rate is at, or about, 600 Hz.

Our studies have shown that the electromagnetic radiation can be either coherent or non-coherent the clinical outcomes are not affected by this parameter.

Preferably the electromagnetic radiation is applied to the affected area for at least 30 seconds and up to a few minutes. A typical exposure time is in the region of 3 minutes, however for deeper wrinkles this time is increased according to the individuals fat layer depth and exposure could be up to 10 minutes.

It should be appreciated that the power source emitting the electromagnetic radiation will have to produce more than the required intensity for the clinical effect since we have shown that approximately 99% of the applied therapeutic amount of light is lost across the skin surface during treatment. Thus the intensity of applied radiation will have to be corrected for when carrying out a treatment.

From the foregoing it is understood that the electromagnetic radiation may be directed to the target site either continuously or in a switched (pulsed) manner. The main benefit of switching enables power conservation and facilities much higher peak power output, thereby improving cosmetic response.

Preferably, the electromagnetic radiation therapy source includes means for reducing the amount of ambient radiation, which impinges on the treatment site.

Preferably, the electromagnetic radiation source is a light emitting diode. The radiation from such devices can be electrically operated or the radiation can be delivered to an applicator via a fibre-optic delivery system.

Preferably, the radiation source emitter includes a PN junction arranged to emit radiation with a wavelength centring at or about the previously mentioned specified wavelengths. A single light diode assembly may include a plurality of orientated junctions. Infrared emitting diodes may be arranged not only to emit radiation at a specific frequency but also to emit a high intensity divergent beam. The divergent light may also be derived from light emitting polymers.

The present invention is concerned with a method of cosmetically treating skin with divergent electromagnetic radiation having a wavelength in the range from visible to infra red and centred around 940 nm, 950 nm, 1040 nm, 1060 nm, 1072 nm or 1267 nm. The electromagnetic radiation is applied at a low intensity such that no thermal damage or heating is caused to the skin or any other tissue or organ around the treatment area. In this way, the method of the present invention differs from the prior art as the effects are non-thermal and avoid thermolysis. In addition the present invention is counter-intuitive to biostimulation since the concept of enhanced replication and synthesis is positively avoided. Indeed we have found that the wavelengths employed in the present invention specifically inhibit DNA synthesis, inhibit collagen production and inhibit fibroblast replication. Our results have shown that the quality of connective tissue between the cells is surprisingly improved by the inhibition of collagen production rather than increasing the collagen density to achieve the desired effect, as per the prior art.

According to a second aspect of the invention there is provided a method of improving elastic characteristics of a superficial area of mammalian skin comprising irradiating the skin with a source of divergent electromagnetic radiation of between 900 nm to 1500 nm.

We have found using the method of the present invention that elastin fibres become less fragmented and more uniform hence improve the elastic characteristics of the skin. For example when treating breast skin we found that not only did the skin elasticity improve but also the tissue tone. We have also found that the method of the present invention improves cell viability.

According to a third aspect of the invention there is provided a method of reducing surface area and volume of tissue of a superficial area of mammalian skin comprising irradiating the skin with a source of divergent electromagnetic radiation of between 900 nm to 1500 nm.

Results obtained by the method of the present invention demonstrate that by reducing skin volume above the eyes and under the eyes we can reduce the sagging appearance of the sides of the face. In this way we show that reduction of tissue volume and surface area of the skin along with improved elastic characteristics provides the desired cosmetic effects.

It will be appreciated that in a fourth aspect of the method of the present invention it may also be used to prevent or reduce or reverse skin damage caused by UV light or photoaging.

According to a fifth aspect of the invention there is provided use of divergent electromagnetic radiation of between 900 nm to 1500 nm for cosmetically treating an area of superficial skin.

Preferably, the second, third, fourth and fifth aspects of the invention further include any one or more of the features hereinbefore described of the first aspect of the invention.

Light therapy, both laser and LED, have been shown to provide clinical benefit in many therapeutic arenas. The effects of light centred around wavelengths of 1072 nm and 880 nm, using a range of single and multiple irradiation protocols, have been assessed for their effect on freshly prepared human lymphocytes stimulated with phytohemagglutinin (PHA). Viable cell numbers remained significantly higher after irradiation with 1072 nm and were significantly lower after 880 nm irradiation compared to untreated controls, following a daily single irradiation over a five day period. In addition, cell numbers were significantly higher after pre-treatment with 1072 nm and exposure to UVA, compared to cells treated with UVA only. Cells irradiated twice on Day 3 post-harvest with various wavebands confirm on Day 5, an increase in % cell viability after exposure to 1072 nm, and 1072 nm alternating with 1268 nm irradiation, and a decrease in % cell viability after 880 nm irradiation alone. These observations lead us to believe that light centred around a wavelength of 1072 nm may be useful in an ex vivo method to improve immune cell viability.

According to a sixth aspect of the invention there is provided an ex vivo method of improving immune cell viability comprising exposing peripheral blood mononuclear cells to divergent electromagnetic radiation of narrow bandwidth centred around a wavelength of 1072 nm.

Preferably, the peripheral blood mononuclear cells are lymphocytes.

Preferably, the peripheral blood mononuclear cells are stimulated with phyto-hemagglutinin (PHA).

It will be appreciated that the cells may then be re-introduced into the individual from which they were harvested so as to boost their immune system.

According to a further aspect of the invention there is provided a portable light emitting device for the cosmetic treatment of skin, the device comprises a power means for supplying power to a light emitting means that produces divergent electromagnetic radiation of between 900 nm to 1500 nm, a flexible or shaped panel through which the light passes and a housing to which the flexible or shaped panel is attached so that the device may be contoured around a part of the body requiring cosmetic treatment.

Preferably, the power means is a battery or is mains electricity.

Preferably, the light emitting device is a LED or more preferably a plurality of LEDs. It will be appreciated that the device of the present invention is not a laser device.

Preferably, the device may also comprise at least one or more PN junctions arranged to emit radiation with a wavelength centring at or about any one or more of the specified wavelengths selected from the group comprising 940 nm, 950 nm, 1040 nm, 1060 nm, 1072 nm and 1267 nm.

BRIEF DESCRIPTION OF THE DRAWINGS

The invention will now be described with reference to the following Figures wherein:

FIG. 10 shows a Western Blot showing the effect of IR treatment upon iNOS protein expression levels PHA blasts were exposed daily to 1×3 min infra red source, IR1072 or IR880 and assayed on Days 3 and 5, for INOS protein expression using quantitative immunoblotting with a selective anti-iNOS antibody (Autogen Bioclear, UK) (Immunoblots were re-probed and standardized with a beta-actin antibody (Sigma, UK). Lane 1, control cells (Day 5); Lane 2, IR1072-treated cells (Day 5); Lane 3, IR880-treated cells (day 5). Data were compared by compared by a multiple ANOVA with a level of significance set at $p<0.01$.

FIG. 11A shows the effects after 2 months of daily treatment with 1072 nm compared to FIG. 11B of the same individual before treatment commenced, FIG. 11C shows a superimposed before picture and a picture after 1 month of treatment of treatment with 1072 nm on the same individual.

FIGS. 13A (before) and 13B shows the effect of multiple treatments and reduction of bags under the eyes.

FIGS. 14A, B and C shows a different individual from FIG. 12 having undergone the same protocol.

DETAILED DESCRIPTION

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

All publications, U.S. patent applications, U.S. patents and other references cited herein are incorporated by reference in their entirety with respect to the text referenced by the citation.

There are several products claiming efficacy in the treatment of lines and wrinkles utilising non-thermal light in the blue, yellow or Red wavelengths. In the present invention we have attempted to identify any physiological response which was wavelength dependant. The wavelengths used ranged from 660 nm to 1268 nm, various restricted bandwidths were examined both alone and in combination. We have found that a single restricted bandwidth of light centred at 1072 nm appeared to have a positive effect on human lymphocytes. This wavelength of light was shown to protect human lymphocytes against the damaging effect of UV radiation, a known photo-ageing agent.

The preferred device to put the method of the invention into practice is a portable light-emitting device 1, which can be either battery or mains operated. The device follows the contours of the area to be treated 2, the face, eyes, arms, thighs or breast.

Figure 1B:
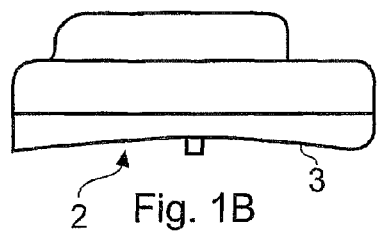
FIG. 1 shows plan (1A), side (1B) and cross-sectional views (1C and 1D) of one of the devices for putting the method of the invention into practice.
Figure 1A:
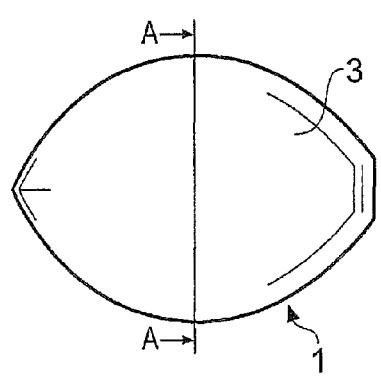
Figure 1C:
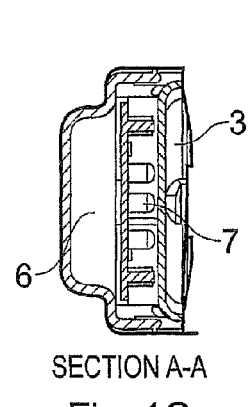
Figure 1D:
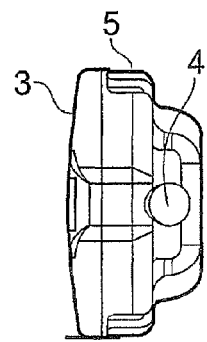
Figure 2:
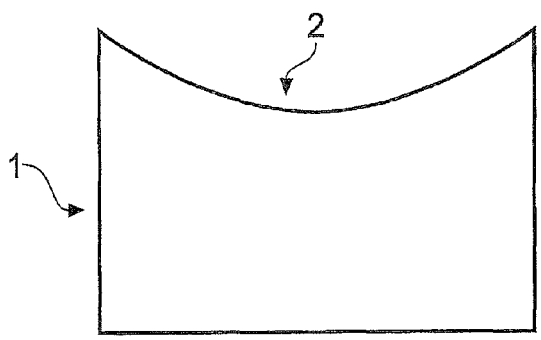
FIG. 2 shows a side view of an alternative of the device for putting the method of the invention into practice.

FIG. 1A shows plan view, side view (1B) and cross-sectional views (1C and 1D) of a portable hand held light emitting device, which has the convenient shape of an eye. The infrared light passes through transparent panel 3 to the skin to be treated. The power supply to the unit is connected through area 4 and the device is held in place by the body 5. Panel 3 is slightly concave to follow the contours of the area to be treated and to avoid undue pressure on the eye when placed over the orbit. Space 6 contains the control electronics, which control the intensity and duration of the treatment cycle. It also houses LEDs 7. FIG. 2 shows an alternative embodiment of the device for placing over a larger part of skin.

Figure 3:
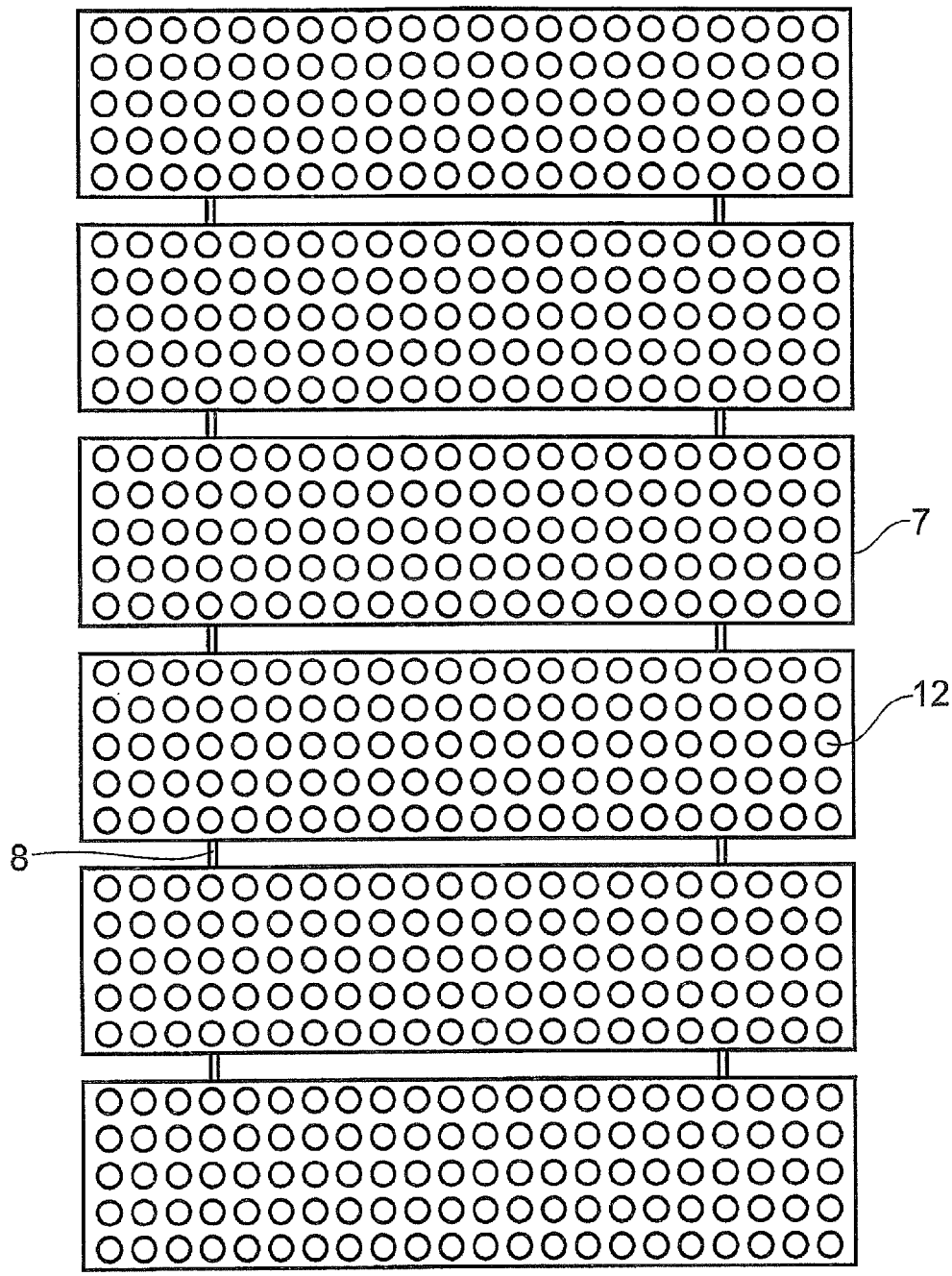
FIG. 3 shows a front.
Figure 4:
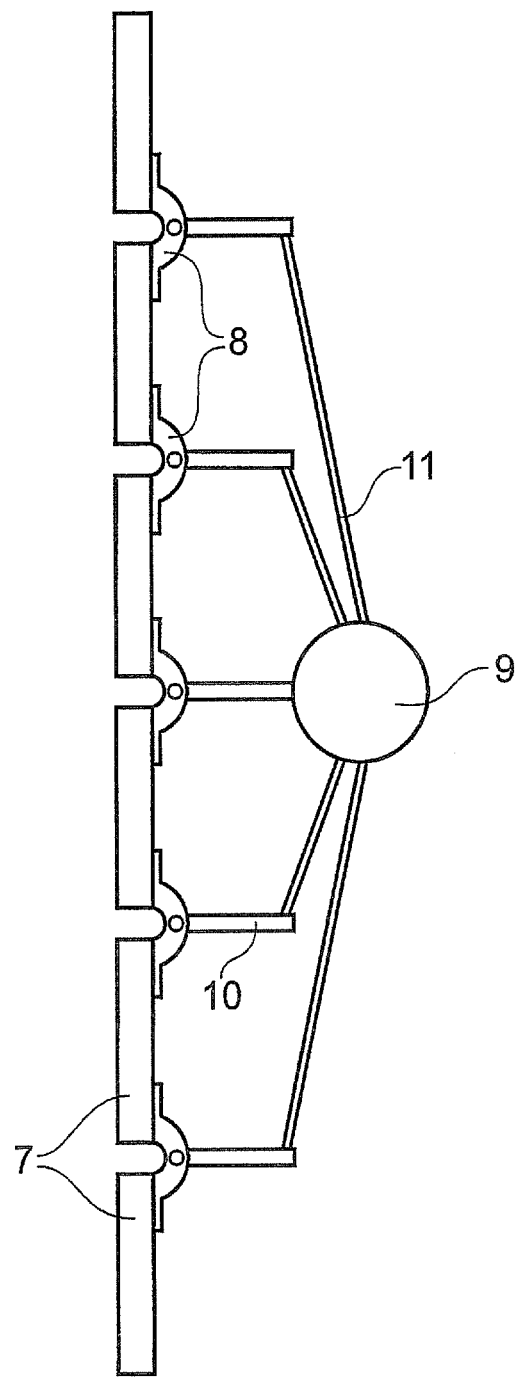
FIG. 4 shows a side and FIG. 5 a rear view of a yet further alternative of the device for putting the method of the invention into practice.
Figure 5:
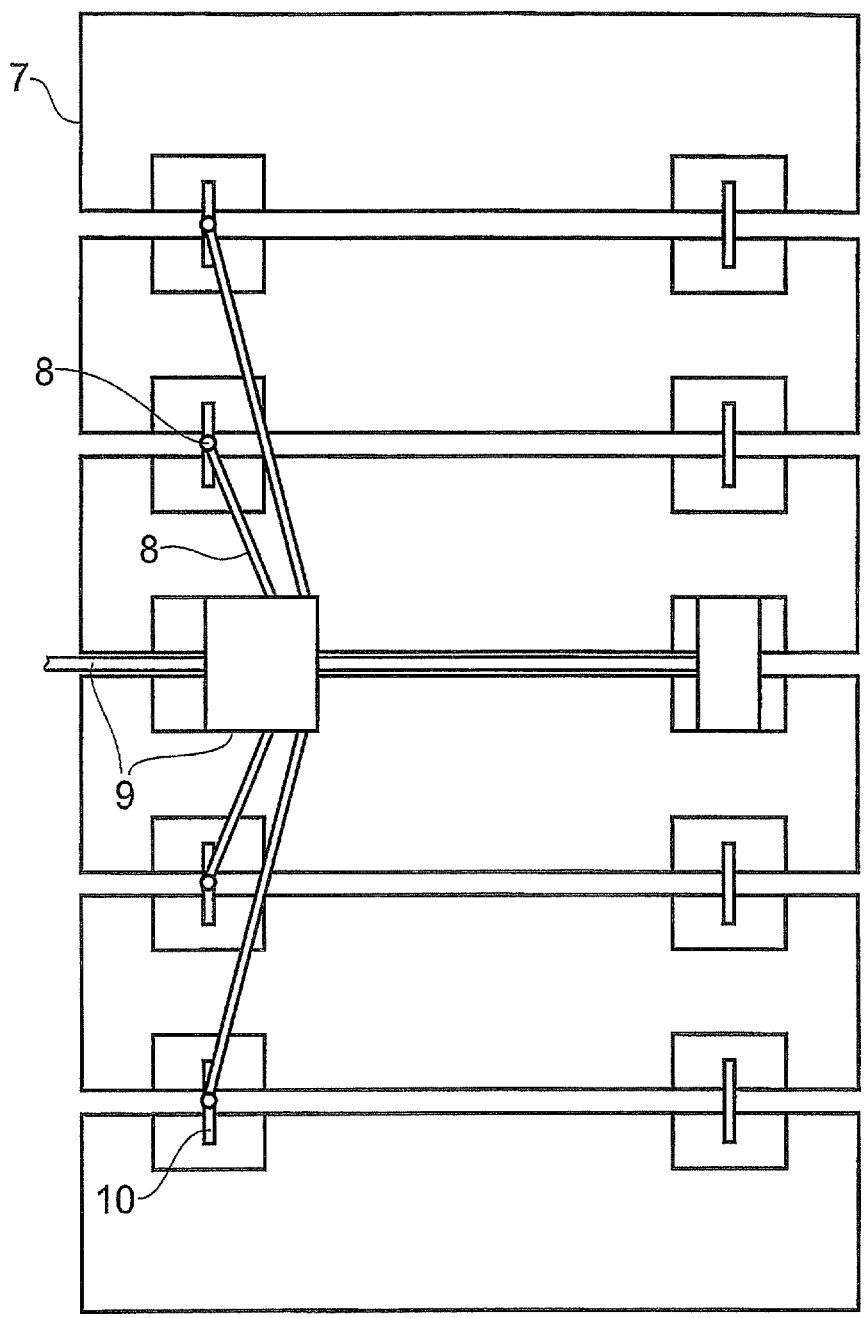

With reference to FIGS. 3 to 5 of the accompanying drawings, a second embodiment in accordance with the present invention is in the form of a multi-panel narrow wavelength radiation source. In this case, a plurality of panels 7 are mounted in a side by side relationship on hinges 8 which, in turn, are connected to a stand 9 by means of arms 10 and 11. The arrangement is such that the panels can move relative to each other and the stand can be adjusted to alter the direction of illumination. The stand either extends from the floor or is attached to a chair or bed.

The front wall of each panel 7 is transparent and, mounted below the front wall, is an array of radiation emitting devices 12.

As with the earlier above described embodiments of the device, this embodiment of the invention includes control electronics to limit the time of the application of the radiation and to monitor the ambient radiation and provide an alarm when the threshold value of the ambient radiation is exceeded.

The devices of the present invention can be used for the cosmetic improvement of cellulite affecting the buttocks and legs, and tissue tone of the breasts, they may also be used to treat the face as a whole.

Methods and Materials
Cell Preparation

Heparinized human whole blood was obtained from healthy volunteers and peripheral blood mononuclear cells (PBMC) were separated using Lymphoprep (Axis-Shield Poc AS, Oslo, Norway) and centrifuged at 400×g for 25 min. The PBMC's were isolated from the interfacial layer, washed twice in RPMI wash without L-glutamine (Gibco™) and resuspended in RPMIcm (RMPI wash+10% v/v Fetal Calf Serum+1% Penicillin/Streptomycin+1% L-Glutamine). Cell density was adjusted accordingly to $1 \times 10^6$ cells/ml with RPMIcm. 100 µl PHA ('Lectin', Sigma) was added to the cells to make PHA Blasts. Cells were incubated at 37° C. in 5% $CO_2$.

Experimental Set-up

The five protocols were set-up as follows:

1. PHA Blasts were exposed to infrared light source, IR1072, on Days 3, 4 and 5 post-harvest, Using 35 mm culture dishes, all cells were exposed to a single 3 min treatment of infrared light. Following daily treatments, individual replicate cell samples were analysed for % cell viability on day 5.

2. PHA Blasts were exposed to IR1072 & IR880 on Day 3 and 5 for 5×3 min treatments and analysed on Day 5. Cell viability and iNOS expression was determined after each treatment on Day 5.

3. PHA Blasts were exposed daily from Day 1 onwards to a single 3 minute dose of IR1072 and IR880. After daily irradiation, cells were analysed for % cell viability.

4. PHA Blasts were exposed to IR1072 on Day 3 for 4×3 min treatment and on Day 4 for a single 3 min treatment. Cells were then left for 4 hours before exposure to UVA for 40 min, and cell viability was then determined.

5. Cells were incubated until Day 3 in tissue culture tubes and exposed to various wavebands for 2×3 minutes on Day 3. Wavebands included IR660 nm, IR880 nm, IR950 nm, IR1267 nm, IR1072 nm, IR1072 alternating with IR1268 nm, IR1072 and IR1267 nm, 1 µs pulsing of IR1072 nm and 7 µs pulsing of IR1072 nm. Cell were analysed for % cell viability immediately after irradiation.

Notably for all protocols used, the temperature of all the dishes was maintained at room temperature throughout the IR and control treatments.

Annexin V Apoptosis Kit

Cell viabilities were analysed using the Annexin V Apoptosis Detection kit (Autogen Bioclear, UK). Apoptosis can be detected by the change in position of phosphatidylserine (PS) in the cell membrane. In non-apoptotic cells, most PS molecules are localised at the inner layer of the plasma membrane, but soon after inducing apoptosis, PD redistributes to the outer layer of the membrane. Exposed PS can be easily detected with Annexin V. Cells with bound Annexin V showed green staining in the plasma membrane. Cells that had lost membrane integrity showed red staining (PI) throughout the cytoplasm and a halo of green staining on the cell surface (plasma membrane). Cells at $1 \times 10^5$-$1 \times 10^6$ per dish were rinsed and resuspended in Assay Binding Buffer. 5 µl of Annexin V and 10 µl of Propidium Iodide (PI) were added to the cells before incubating at room temperature in the dark for 15-30 min. Cells were observed under a dual filter set for FITC & rhodamine using fluorescence microscopy, and counted blind by at least two observers.

Western Blotting Analysis

Thawed cell pellet suspensions were homogenised on ice with a Dounce homogenises. The protein levels in the cell suspension were determined using the Lowry Assay using bovine serum albumin as a standard. Protein levels were adjusted to 10 µg protein was loaded in each lane. Standard electrophoresis was performed using a 6% polyacrylamide gel. Following electrophoresis, the protein was transferred to nitrocellulose (NC) membrane for 2.5 hours at 50V. The NC membrane was blocked with 5% no-fat dried milk in 1×Tris buffered saline (TBS) containing 0.2% Tween 20 (Sigma, UK) for 1 hour at room temperature. The NC membrane was incubated with primary antibody iNOS (dilution 1:2500)

overnight at 4° C. The NC membrane was washed 4×10 min with wash buffer (2.5% non-fat dried milk, 0.2% Tween 20 in TBS) and incubated with anti-rabbit horseradish peroxidase-linked secondary antibody (dilution 1:2000) for 1 hour. The NC membrane was washed 4×10 min with wash buffer. The protein bands from the NC were visualised using a substrate of 68 mM luminol, 1.25 mM p-couramic acid, 30% hydrogen peroxide. The immunoblot was exposed to Hyperfilm™ for 3 min in a film cassette and were developed and fixed at room temperature. The protein bands were quantified using an ImageQuant® densitometer in the linear range of the film, to determine the relative iNOS expression. Optical density values (standardized with beta-actin) were compared using a multiple ANOVA with a significance level of $p<0.05$. Data were obtained from n=3 individual replicate experiments.

Statistics

Apoptosis was measured using % cell viability, that is,

% cell viability=[(No. of viable cells)/(No. of total cells)]*100

Data are given as the mean±standard deviation.

Comparisons between control and treated cells were made by a multiple ANOVA and expressed as mean±SD, with a confidence interval of 95%. Statistical analysis was carried out using Prism 3.2.

Light Sources

Both the 880 nm and 1072 nm light sources emitted multimode light of bandwidth less than 50 nm, continuous mode of optical power 5 mw/sq cm.

Human Studies

The wavelengths used ranged from 660 nm to 1268 nm, various restricted bandwidths were examined both alone and in combination.

40 Volunteers were recruited from the general population, aged between 45 years and 65 years, 38 females, 2 males. Each individual was photographed using the fixed lighting and fixed distance. The views taken were: left of centre of the face; right of centre of the face; left profile of the face and; right profile of the face. Constant distance and lighting facilitated a direct comparison between the "Before" and "After" photographs.

When taking the "After" photographs it was ensured that the eyes were open a similar amount as compared to the "Before" photograph. This then allowed the comparison of skin folds above and the bags below the eyes. The participants were specifically asked not to smile or to have any expression on their face when the photographs were taken. The participants were each given an active device and asked to treat the skin area around the eyes for approximately 30 minutes each day (15 minutes per eye area). The skin around the eyes was chosen as it is more mobile and more likely to demonstrate an improvement in the elasticity of the skin.

EXAMPLE 1

Using a range of protocols, IR1072 treatment consistently elicited a significant protective effect upon PHA blast survival. In contrast, IR 880 was consistently cytotoxic compared to control and IR1072 treated cells.

Figure 6:
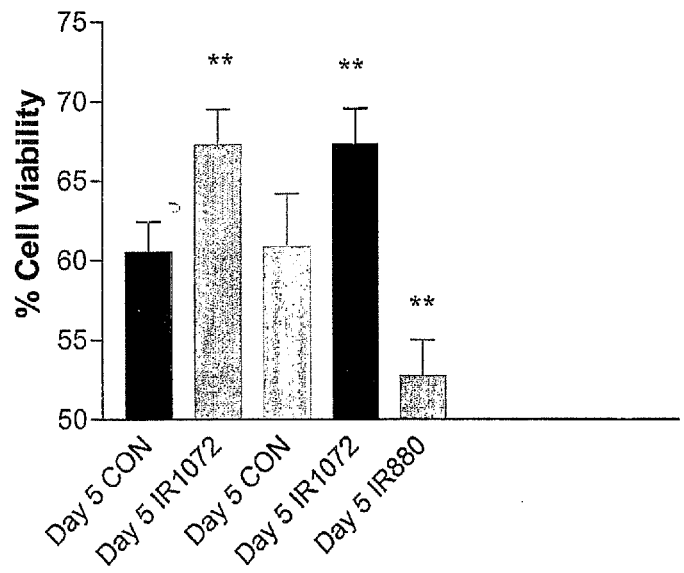
FIG. 6, columns 1 and 2 show the % cell viability of PHA blasts following a single 3 min treatment of IR1072 on Day 3 and Day 5 before testing for apoptosis on Day 5. Data were compared to respective controls, and analysed using an ANOVA, where $*p<0.05$. Columns 3, 4 and 5 show the % cell viability of PHA Blasts following multiple 5×3 min treatments of IR1072 & IR880 on Day 3 and Day 5, before testing for cell viability on Day 5. Data were compared to respective controls on Day 5, and analysed using an ANOVA, where $**p<0.01$
Figure 7:
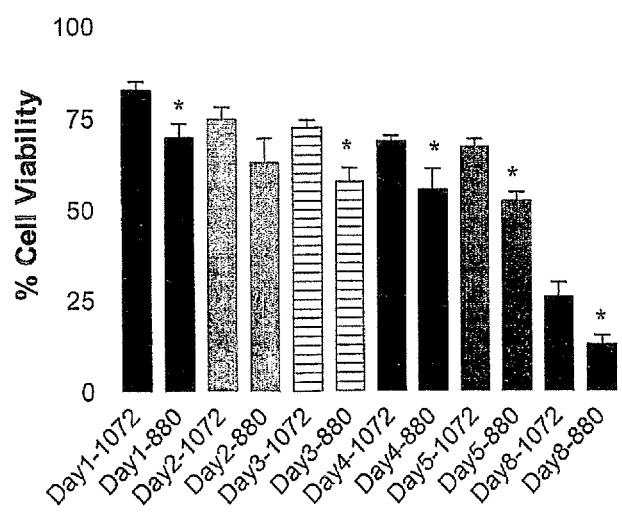
FIG. 7 shows the % cell viability of PHA Blasts following daily single 3 minute treatments irradiated with either IR1072 or IR880. Cell viability was determined using the Annexin V apoptosis kit. IR1072 data were analysed compared to respective IR880 data, using an ANOVA, where significant differences were seen on Days 1, 3, 4 and 5 $*p<0.01$, and a trend to significance on Day 2.
Figure 8:
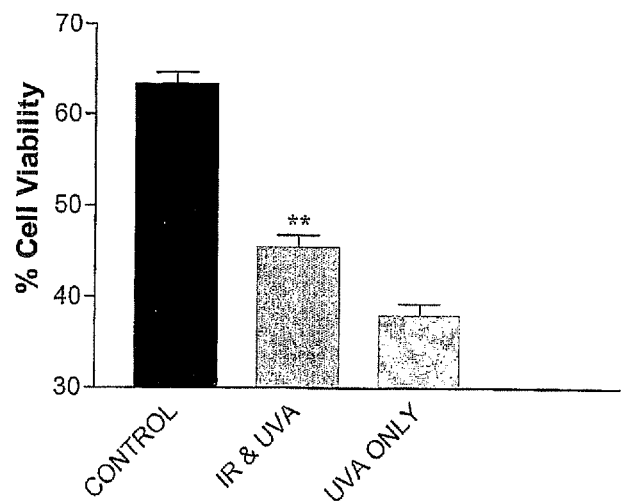
FIG. 8 shows PHA blasts that were pre-treated 4×3 min on Day 3, and 1×3 min on Day 4 with IR1072, and then cells were incubated for 4 hours before UVA exposure for 40 min. Samples were then assayed for cell viability. Data were analysed and compared to UV treated alone using an ANOVA, where $p<0.01$
Figure 9:
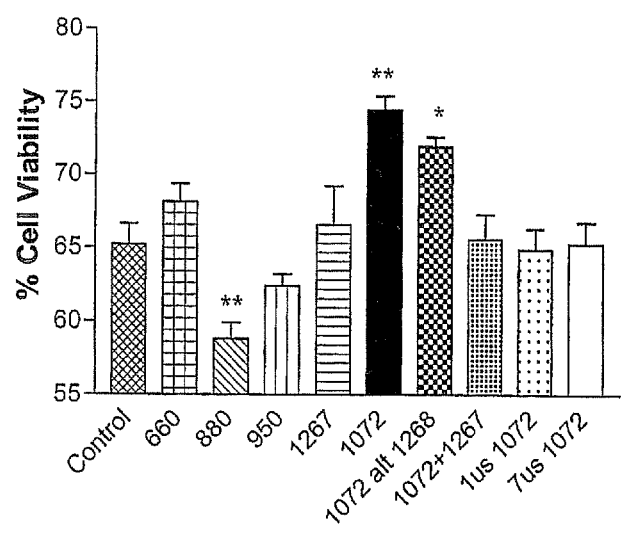
FIG. 9 shows the effect of various wavebands on PHA Blasts treated on Day 3 for 2×3 minutes and analysed. Data were analysed and compared to the untreated control using a multiple ANOVA, where $p<0.01$
Figure 12:
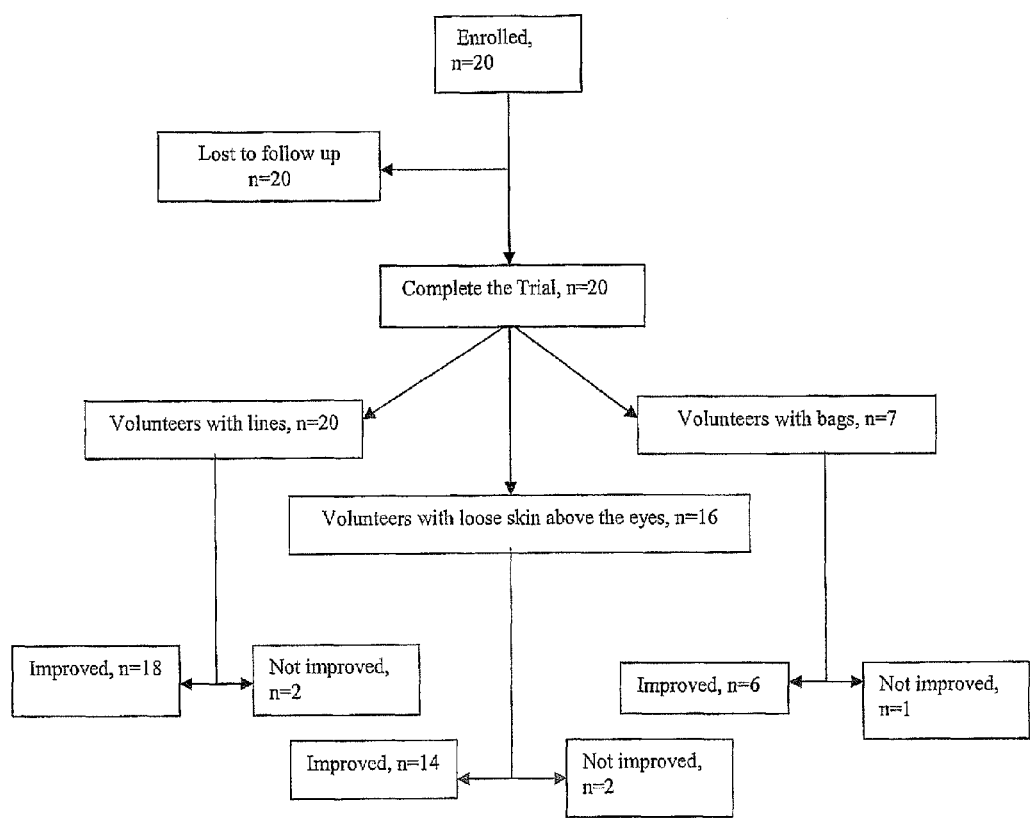
FIG. 12 shows a schematic representation of the protocol for the human studies.

Following irradiation with IR1072, % cell viability significantly increased on Day 5 ($p<0.05$) compared to the control data following both a single and multiple 5×3 min treatment protocol on Day 3 and 5 (FIG. 6). In the next protocol, cells irradiated with 5×3 min of IR1072 and IR880, the % cell viability significantly decreased after treatment with IR880 both on Day 5 ($p<0.01$) compared to cells treated with IR1072 (FIG. 6). The daily treatment protocol elicited a significant decrease in % cell viability for IR880 treated cells over an 8 day period [Day 1 ($p<0.01$), Day 3 ($p<0.01$), Day 4 ($p<0.05$), Day 5 ($p<0.05$) and Day 8 ($p<0.05$)], compared to those irradiated with IR1072 (FIG. 7), in parallel experiments. After pre-treatment with IR1072, and subsequent exposure to UVA, ° A) cell viability remained significantly higher ($p<0.01$) compared to cells treated only with UVA (FIG. 8). Following irradiation with various wavebands, again cells exposed to IR880 showed significant decrease in % cell viability ($p<0.01$), whereas the % cell viability was higher following treatment with 181072 ($p<0.01$) and alternate IR1072 IR1268 waveband light ($p<0.01$), all compared to untreated controls (FIG. 9). All other wavelengths and conditions tested had no significant effect upon cell viability.

Although wavelengths in the 855-905 nm range may stimulate fibroblast proliferation we have found that light in this range appears to be lymphotoxic. The cytotoxic and protective effects upon the cells are rapid as the analysis was carried out within 2 hours of exposure to the IR light, and both effects were long lasting, being observed at least 2 days post-treatments. Our studies clearly demonstrate that light in the 1050 nm-1100 nm range improves cell viability following both single and multiple treatment protocols. Maintaining lymphocyte viability in the presence of adverse factors is of significance as bacterial endo- and exo-toxins are leucotoxic factors, the effect of which, may be reduced by the irradiation of the inflammatory cells by 1072 nm±25 nm light. It has long been postulated that IR light has a protective effect against UVA, however the exact range of wavelengths has been unknown. These present results suggest 1072 nm±25 nm light is protective against some of the damaging effects of UVA.

EXAMPLE 2

Nitric oxide has been shown to be a potent inhibitor of apoptosis in a variety of cell types. NO diffuses very rapidly both through water and cell membranes, and iNOS is produced more rapidly and efficiently than eNOS and nNOS. iNOS can function without the elevation of intracellular calcium levels and its activity is rapidly inducible in immune cells, for example, primarily activated monocytes and macrophages, following exposure to cytokines and microbial products.

In order to ellucidate the potential mechanism underlying the observed long-lasting cytoprotection elicited by exposure to IR1072, quantitative immunoblotting was performed probing the expression of iNOS, in comparison to control and IR880 nm. Following pre-treatment with IR1072, a significant increase of 4.9±2.1-fold ($p<0.05$) in INOS immunoreactivity was detected at Day 5, compared to control. In contrast, no significant increase in iNOS was observed with IR880 (2.1±2.2-fold for Day 5) ($p>0.05$), performed in parallel studies (FIG. 10).

Biochemically, these present results show that iNOS has been upregulated in a wave-length dependent fashion, in comparison to untreated controls. NO is believed to act as an inhibitor of apoptosis by two distinct mechanisms: firstly through a cGMP-dependent mechanism where NO acts either at the level of caspase-3-like protease activation or upstream of this event to prevent the activation of the protease; secondly, NO also inhibits the activity of the caspase-3-like protease by S-nitrosylation of the enzyme. Suppression of caspase-3-like activity then rescues the cell from programmed cell death.

EXAMPLE 3

Following treatment of the skin of the face and eyes with the light source we observed a reduction in wrinkle depth, length and area, we also observed a reduction in the surface area of the skin above the eye and a reduction in the prominence of the bags under the eyes. To ensure a reduction in artifact to the minimum a constant illumination light box was used. This facilitated a constant distance of the lens of the camera from the subject and a constant exposure. The subjects were required to focus on the same point and rest their chins on a fixed point with their nose touching a string to ensure minimal rotation between photographs. The subjects were then given a light source to treat themselves at least once a day but preferably twice a day. After a month the initial follow up photographs were taken, followed by another series of photographs at 2 months. When taking the photograph it was essential that in all cases at all times the face was devoid of expression, the eyes were open the same amount, enabling direct comparision of the skin above the eye, and the gaze directed at the same spot on the light box in all cases. 4 views were taken, Left Front, Right Front, Left profile and Right profile. This facilitated the direct comparision of bags under the eyes and wrinkle length and depth. Wrinkles that were not the perpendicular or horizontal plane was not examined at slight differences in rotation would create artifactual differences. We have also observed improvement of tissue and muscle tone on various other parts of the body where the electromagnetic cosmetic treatment has been applied. The results show a qualitative improvement in reducing the visible signs of aging, reduction in redundant skin affecting the upper eye lids, maintaining facial tissue tone and hence maintaining youthful naso-labial folds and contours of the face.

The method of the invention improved skin texture and contours resulting in smoother skin. These effects can be maintained for up to one to three months after treatment is discontinued and are able to reverse the visible signs of aging by as much as 10 years in some cases.

When applying the light to the thighs and buttocks there was a significant improvement in the observed cellulite, a reduction in the degree the buttocks sagged under the influence of gravity.

With reference to FIG. 11A there is shown the effects after 2 months of daily treatment with IR 1072 nm compared to FIG. 11B of the same individual before treatment commenced, FIG. 11C shows a superimposed before picture and a picture after 1 month of treatment of treatment with IR 1072 nm on the same individual. We have observed after 1 month of treatment the skin folds above the eye lid can be directly compared as the upper lid cuts the cornea at the same place and the light reflexes on the cornea are identical in both control and test cases (FIG. 11 C). We have observed that the upper lid sags less following treatment. The sagging is further improved following two months of treatment (FIG. 11 A).

EXAMPLE 4

With reference to FIG. 13A, there is shown a side profile of an individual prior to treatment and in FIG. 13B, the same individual post treatment. The individual had an identifiable landmark of a pigmented lesion inferior to the corneal limbus. A line was drawn perpendicular to the black marker line and the following measurements were made:

|  | FIG. 13A | FIG. 13B |
|---|---|---|
| 1. Tip of nose: | 34.2 mm | 38.3 mm |
| 2. From line to pigmented lesion: | 20.3 mm | 28.6 mm |
| 3. From line to bag (7 mm below lid) | 18 mm | 23.2 mm |

Adjustment due to scale variation (distance to nose) was made for the line to pigmented lesion: (38.3/34.2)×20.3=22.7 mm and from the line to bag: (38.3/34.2)×18=20.2 mm

| Corrected Results | | |
|---|---|---|
|  | Before | After |
| Line to Pigmented Lesion | 22.7 mm | 28.6 mm |
| Line to Bag | 20.2 mm | 23.2 mm |

Utilising the above technique the bag reduction was measured in 8 volunteers. 7 demonstrated a reduction in the size of the bags under the eye.

EXAMPLE 5

Ensuring the aperture of the eyes was identical in both the before and after FIG. 14C, a part of one eye is cut in the "before" picture (FIG. 14A) and merged with the complimentary side of the eye from the "after" picture (FIG. 14B). The improvement in skin quality can easily be seen.

The outcome measures, bag size and measurement of loose skin olds removed the variability inherent in merely assessing wrinkles around the eyes.

|  | Wrinkles | Bags under eyes | Loose skin above eye lid |
|---|---|---|---|
| Improved | n = 18 | n = 6 | n = 14 |
| Not Improved | n = 2 | n = 1 | n = 2 |
|  | p = 0.0004 | p = 0.1 | p = 0.004 |

19 out of the 20 participants involved in the study were satisfied that the 1072 nm light therapy was effective, p=0.00004.

Utilising the baseline photographs as the control aspect of the cosmetic trial the above data demonstrates the efficacy of the method and device of the present invention. Daily treatments resulted in the majority of participants achieving a positive outcome with a more youthful appearance.

The invention claimed is:

1. A method of cosmetically treating a superficial area of mammalian skin comprising irradiating the skin with a source of divergent electromagnetic radiation centered around 1072 nm,
   wherein the cosmetic treatment provides at least one effect selected from the group consisting of:
   (i) reducing, alleviating, removing or diminishing wrinkles or fine lines;
   (ii) reducing skin surface area;
   (iii) rejuvenating skin;
   (iv) retarding or reversing visible signs of aging; and
   (v) improving skin elasticity or elastic characteristics of skin, tone, texture and appearance,
   wherein the electromagnetic radiation has a bandwidth in a range of about 10 to 120 nm.

2. The method according to claim 1, wherein the skin comprises the outermost epidermis, basal layer and dermis of face, breast, arm, buttock, thigh, stomach or neck.

3. The method according to claim 1, wherein the divergent light is in a range of between 10° to 50°.

4. The method according to claim 1, wherein the electromagnetic radiation is continuous or pulsed.

5. The method according to claim 4, wherein when the electromagnetic radiation is continuous, the intensity is in a range from at least 500 μWatts/cm$^2$ to 500 mWatts/cm$^2$.

6. The method according to claim 4, wherein when the electromagnetic radiation is pulsed, the intensity is at least 500 μWatts/cm$^2$ peak power and the average power is up to 500 mWatts/cm$^2$.

7. The method according to claim 6, wherein when the electromagnetic radiation is pulsed, the average power of the intensity is in a range of from 50 to 100 μWatts/cm$^2$.

8. The method according to claim 4, wherein when the electromagnetic radiation is pulsed, it is applied for a period of time in a range from at least 10 to 15 μseconds.

9. The method according to claim 4, wherein when the electromagnetic radiation is pulsed, the frequency/repetition rate is in the range from 300 to 900 Hz.

10. The method according to claim 9, wherein the frequency/repetition rate is at, or about, 600 Hz.

11. The method according to claim 1, wherein the electromagnetic radiation is applied to the skin for a period of time in a range from at least 30 seconds to a few minutes.

12. The method according to claim 1, wherein the electromagnetic radiation source is a light emitting diode.

13. The method according to claim 1, wherein the radiation source emitter comprises at least one or more PN junctions arranged to emit radiation with a wavelength centered at or about 1072 nm.

14. The method according to claim 13, wherein the wavelength has a waveband of about 50 nm.

* * * * *